(12) United States Patent
Shindo

(10) Patent No.: US 11,805,976 B2
(45) Date of Patent: Nov. 7, 2023

(54) SLIDER AND SURGICAL INSTRUMENT

(71) Applicant: RIVERFIELD INC., Tokyo (JP)

(72) Inventor: Koki Shindo, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 0 days.

(21) Appl. No.: 17/606,934

(22) PCT Filed: Jan. 9, 2020

(86) PCT No.: PCT/JP2020/000495
§ 371 (c)(1),
(2) Date: Oct. 27, 2021

(87) PCT Pub. No.: WO2021/140623
PCT Pub. Date: Jul. 15, 2021

(65) Prior Publication Data
US 2022/0211402 A1    Jul. 7, 2022

(51) Int. Cl.
| | |
|---|---|
| *A61B 17/29* | (2006.01) |
| *B25J 17/00* | (2006.01) |
| *A61B 1/00* | (2006.01) |
| *A61B 34/00* | (2016.01) |
| *B25J 15/02* | (2006.01) |

(52) U.S. Cl.
CPC ............ *A61B 1/00* (2013.01); *A61B 1/00064* (2013.01); *A61B 17/2909* (2013.01); *A61B 34/71* (2016.02); *A61B 2017/2902* (2013.01); *B25J 15/0233* (2013.01); *B25J 17/00* (2013.01)

(58) Field of Classification Search
CPC ... A61B 1/00; A61B 1/00064; A61B 17/2909; A61B 2017/2902; A61B 34/71; B25J 15/0233; B25J 17/00
See application file for complete search history.

(56) References Cited

U.S. PATENT DOCUMENTS

| | | |
|---|---|---|
| 5,325,866 A | 7/1994 | Krzyzanowski |
| 2004/0049205 A1 | 3/2004 | Lee et al. |
| 2008/0195144 A1 | 8/2008 | Hashimoto |
| 2010/0082041 A1 | 4/2010 | Prisco |
| 2015/0238225 A1 | 8/2015 | Sekino et al. |
| 2015/0265355 A1 | 9/2015 | Prestel et al. |
| 2016/0296216 A1 | 10/2016 | Nicholas et al. |
| 2017/0095922 A1 | 4/2017 | Licht et al. |

(Continued)

FOREIGN PATENT DOCUMENTS

| | | |
|---|---|---|
| CN | 101237824 A | 8/2008 |
| CN | 102171006 A | 8/2011 |

(Continued)

OTHER PUBLICATIONS

Office Action dated Mar. 25, 2022, issued in Chinese Application No. 202080031994.7.

(Continued)

*Primary Examiner* — Scott Luan
(74) *Attorney, Agent, or Firm* — Sughrue Mion, PLLC

(57) ABSTRACT

A slider is provided. A slider of the present disclosure includes a slider body disposed to be movable in a linear direction relative to a surgical instrument, and two holders disposed on the slider body for holding ends of a wire between the two holders to retain the wire in an annular shape. At least a first holder of the two holders is provided with an insertion hole for inserting and passing the ends of the wire toward an outside from between the two holders.

20 Claims, 6 Drawing Sheets

(56) References Cited

U.S. PATENT DOCUMENTS

2019/0167365 A1   6/2019  Chaplin et al.
2020/0352669 A1  11/2020  Marshall et al.

FOREIGN PATENT DOCUMENTS

| | | |
|---|---|---|
| CN | 102204807 A | 10/2011 |
| CN | 104873266 A | 9/2015 |
| CN | 105287002 A | 2/2016 |
| CN | 106037832 A | 10/2016 |
| CN | 108472025 A | 8/2018 |
| CN | 108882934 A | 11/2018 |
| CN | 208511177 U | 2/2019 |
| CN | 209004599 U | 6/2019 |
| JP | 3-75707 U | 7/1991 |
| JP | 4-210393 A | 7/1992 |
| JP | 2009-269156 A | 11/2009 |
| JP | 5542288 B2 | 7/2014 |
| WO | 2012/043463 A1 | 4/2012 |
| WO | 2018/020251 A1 | 2/2018 |
| WO | 2019/028564 A1 | 2/2019 |
| WO | 2019/244799 A1 | 12/2019 |

OTHER PUBLICATIONS

Translation of the Written Opinion of the International Searching Authority dated Mar. 24, 2020 in International Application No. PCT/JP2020/000495.
International Search Report for PCT/JP2020/000495 dated Mar. 24, 2020 (PCT/ISA/210).
Extended European Search Report dated Jun. 22, 2022 in European Application No. 20911706.8.

SLIDER AND SURGICAL INSTRUMENT

CROSS REFERENCE TO RELATED APPLICATIONS

This application is a National Stage of International Application No. PCT/JP2020/000495 filed Jan. 9, 2020, the entire contents of which being herein incorporated by reference in its entirety.

TECHNICAL FIELD

The present disclosure relates to a slider and a surgical instrument.

BACKGROUND ART

In recent years, medical treatments using robots have been proposed to reduce a burden on operators and to save labor in medical facilities. In the surgical field, proposals have been made for medical robots that use a multi-degree-of-freedom manipulator with a multi-degree-of-freedom arm that is remotely controllable by an operator to treat a patient.

A surgical instrument used for treatment of a patient is attached to the medical robot. A driving force for operating the surgical instrument is transmitted to the surgical instrument from the medical robot. The driving force transmitted to the surgical instrument is transmitted to an operating part of the surgical instrument through a wire disposed inside the surgical instrument (see Patent Document 1, for example).

PRIOR ART DOCUMENTS

Patent Documents

Patent Document 1: Japanese Patent No. 5542288

SUMMARY OF THE INVENTION

Problems to be Solved by the Invention

Patent Document 1 discloses a configuration in which a wire is annularly disposed, and the annular wire is wound around rotating parts such as pulleys provided at least in an operating part of a surgical instrument. In this configuration, a driving force is transmitted to the rotating parts of the operating part by rotational movement of the wire.

When a driving force is transmitted by winding an annular wire around rotating parts such as pulleys, it is preferable to apply a desired tension to the annular wire in order to transmit the driving force. Although it is conceivable to provide a mechanism for applying tension to the annular wire, there has been a problem that addition of the mechanism complicates the structure of the surgical instrument. In a case where a mechanism for applying tension is not provided, there has been a problem that it is difficult to apply a desired tension to the annular wire.

It is desirable that the present disclosure provide a slider and a surgical instrument that facilitate arrangement of a wire in an annular shape by applying a desired tension.

Means for Solving the Problems

A slider according to a first aspect of the present disclosure includes a slider body disposed to be movable in a linear direction relative to a surgical instrument, and two holders disposed on the slider body for holding ends of a wire between the two holders to retain the wire in an annular shape. At least one of the two holders is provided with an insertion hole for inserting and passing the ends of the wire toward an outside from between the two holders.

A surgical instrument according to a second aspect of the present disclosure includes: the slider according to the first aspect of the present disclosure; a surgical instrument body that accommodates the slider; and a movable part driven by a driving force transmitted by the slider.

With such a configuration, tension is applied to the annular wire by inserting the ends of the wire into the insertion hole and pulling the both ends. By bringing the two holders close to each other in a state where tension is applied to the annular wire, the wire can be held between the two holders. Hence, a desired tension can be applied to the annular wire without providing a mechanism for applying tension to the annular wire, and a desired tension can be easily applied to the annular wire.

In the first aspect of the disclosure, it is preferable that the configuration further includes: two protrusions protruding from the slider body to a side where the two holders are disposed, the two holders being disposed between the two protrusions; and a guide provided in the protrusion for guiding the wire to the two holders.

With such a configuration, the positions of the two holders relative to the slider body can be stabilized reliably. Further, by guiding the wire to the holder using the guide provided in the protrusion, the position of the wire relative to the holder can be easily stabilized. In particular, even when the slider body causes relative movement in the linear direction, the position of the wire relative to the holder can be easily stabilized.

In the first aspect of the disclosure, it is preferable that the guide has the shape of a groove, which is formed in the protrusion and which extends toward the two holders, and the guide is provided with an inclined part, in which a width of the groove narrows toward the two holders.

With such a configuration, it is easy to dispose the wire in the guide. Additionally, it is easy to curb an increase in stress acting on a contact portion between the wire and the guide when the slider body causes relative movement in the linear direction.

In the first aspect of the disclosure, it is preferable that the configuration further includes a fastener for fixing the two holders so that the two holders are disposed on the slider body and so that the wire is held between the two holders.

With such a configuration, it is easy to perform the work of fixing the two holders at desired positions of the slider body and the work of fixing the two holders with the wire held between the two holders. Additionally, both works can be performed simultaneously.

Effects of the Invention

With the slider of the first aspect and the surgical instrument of the second aspect of the present disclosure, ends of the wire are inserted into the insertion hole and the wire can be held between the two holders while applying tension to the wire, whereby an effect of easily arranging the wire in an annular shape by applying a desired tension is obtained.

EXPLANATION OF REFERENCE NUMERALS

1 . . . surgical instrument, 11 . . . joint (movable part), 20 . . . surgical instrument body, 30 . . . slider, 31 . . . slider body, 32 . . . protrusion, 34, 134 . . . guide, 35 . . . inclined part, 41 . . . holder, 42 . . . insertion hole, 45 . . . fastener, 51 . . . wire

MODE FOR CARRYING OUT THE INVENTION

A surgical instrument according to an embodiment of the present disclosure will be described with reference to FIGS. 1 to 6. A surgical instrument 1 of the present embodiment is a surgical instrument held by a multi-degree-of-freedom manipulator having a remotely controllable multi-degree-of-freedom arm. The surgical instrument 1 may have a configuration such as forceps used for treatment of a patient such as endoscopic surgery.

Figure 1:
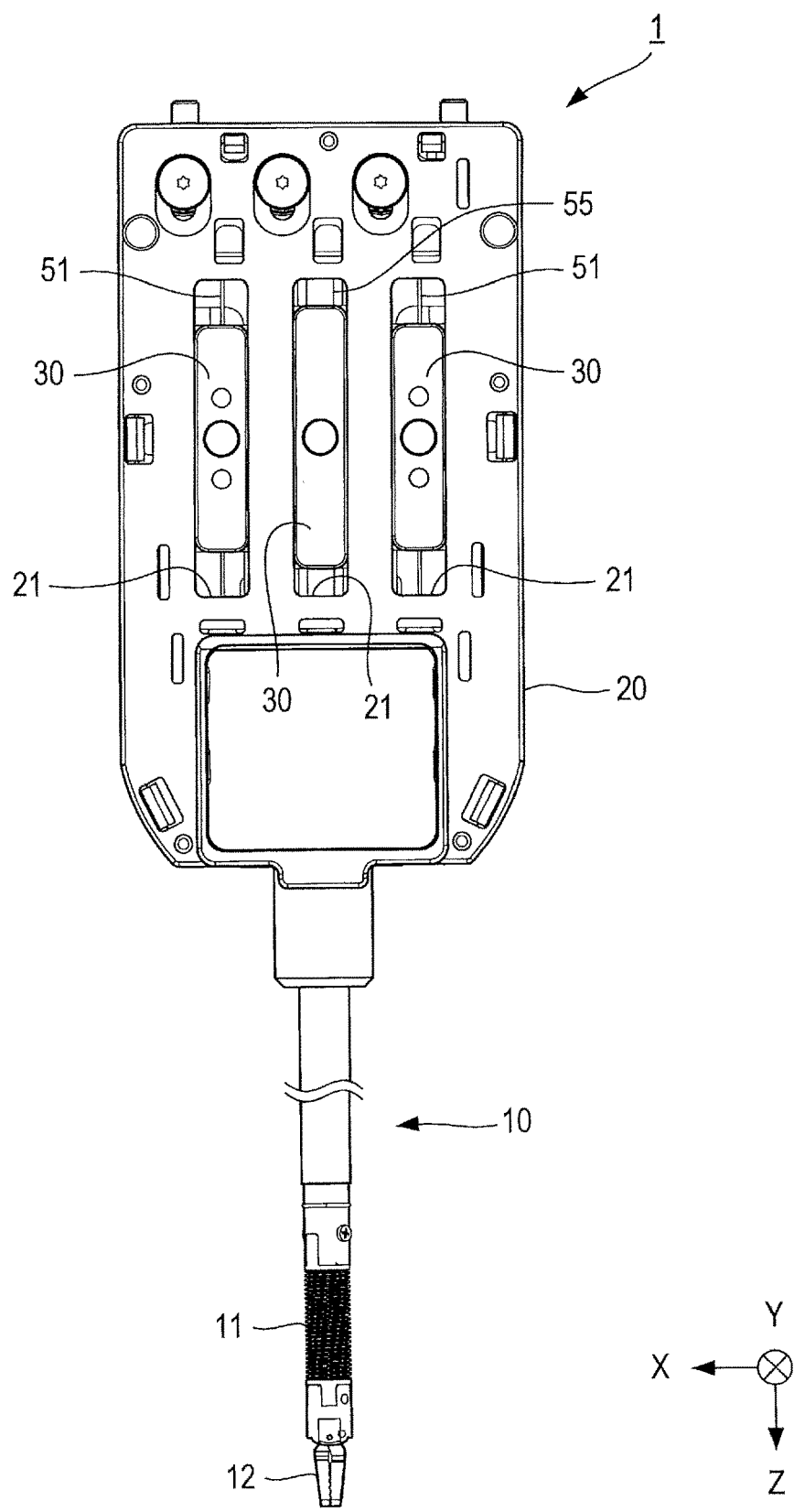
FIG. 1 is a diagram illustrating an embodiment of a surgical instrument of the present disclosure.

As illustrated in FIG. 1, the surgical instrument 1 is provided with a shaft 10 and a surgical instrument body 20.

Note that in the present embodiment, for ease of description, a direction in which the shaft 10 extends is defined as the Z axis, and a direction from the base toward the tip end of the shaft 10 is defined as the positive direction. Additionally, the description will be given assuming that a direction orthogonal to the Z axis and in which multiple later-described sliders 30 are arranged is the X axis, and the left direction of the positive direction of the Z axis is the positive direction of the X axis. Further, the description will be given assuming that a direction orthogonal to the Z axis and the X axis is the Y axis, and a direction from a surface of the surgical instrument body 20 on which the sliders 30 are arranged toward the opposite surface is the positive direction of the Y axis.

The shaft 10 is a member extending in the positive direction of the Z axis from the surgical instrument body 20, and is a rod-shaped member to be inserted into the body of the patient. The shaft 10 has a columnar or cylindrical shape.

A joint (corresponding to movable part) 11 and forceps 12 are provided at an end of the shaft 10 in the positive direction of the Z axis.

The joint 11 is capable of changing the direction of the forceps 12 by a driving force transmitted from a later-described slider 30. The specific configuration of the joint 11 is not particularly limited, and may be a general configuration.

The forceps 12 have a configuration of general forceps for treating a patient. Note that while the present embodiment describes an example in which the forceps 12 are disposed at the tip end of the shaft 10, other instruments used for treatment of a patient may be disposed at the tip end of the shaft 10.

As illustrated in FIG. 1, the surgical instrument body 20 is provided with multiple (three in present embodiment) driven grooves 21 (hereinafter simply referred to as one driven groove 21) and multiple (three in present embodiment) sliders 30 (hereinafter simply referred to as one slider 30).

The driven groove 21 is a long hole provided in an end surface of the surgical instrument body 20 on the negative direction side of the Y axis of two surfaces of the surgical instrument body 20 perpendicular to the Y-axis direction. In other words, the driven groove 21 is a long hole provided on an attachment/detachment surface between the main body 20 and the multi-degree-of-freedom manipulator. Additionally, the driven groove 21 extends along the Z axis.

Three driven grooves 21 are arranged side by side at equal intervals in the X-axis direction. The number of the driven grooves 21 can be determined on the basis of the movement (movement based on required specifications) of the joint 11 and/or the forceps 12, for example. Depending on the required specification, the number of driven grooves 21 may be more or less than three.

The slider 30 is configured to receive a driving force transmitted from the multi-degree-of-freedom manipulator and to transmit the driving force to the joint 11 and the forceps 12. Additionally, the slider 30 is attachable to and detachable from the multi-degree-of-freedom manipulator.

One slider 30 is disposed in each of the three driven grooves 21, and the slider 30 is disposed to be movable in the Z-axis direction inside the driven groove 21.

Among the three sliders 30, two sliders 30 disposed at a first end and a second end along the X-axis direction are configured to transmit driving force to the joint 11. Specifically, a wire 51 for transmitting driving force is disposed on each of the two sliders 30. Among the three sliders 30, the slider 30 disposed at the center is configured to transmit a driving force to the forceps 12. Specifically, a rod 55 that transmits the driving force to the forceps 12 is disposed on the slider 30 at the center.

Figure 2:
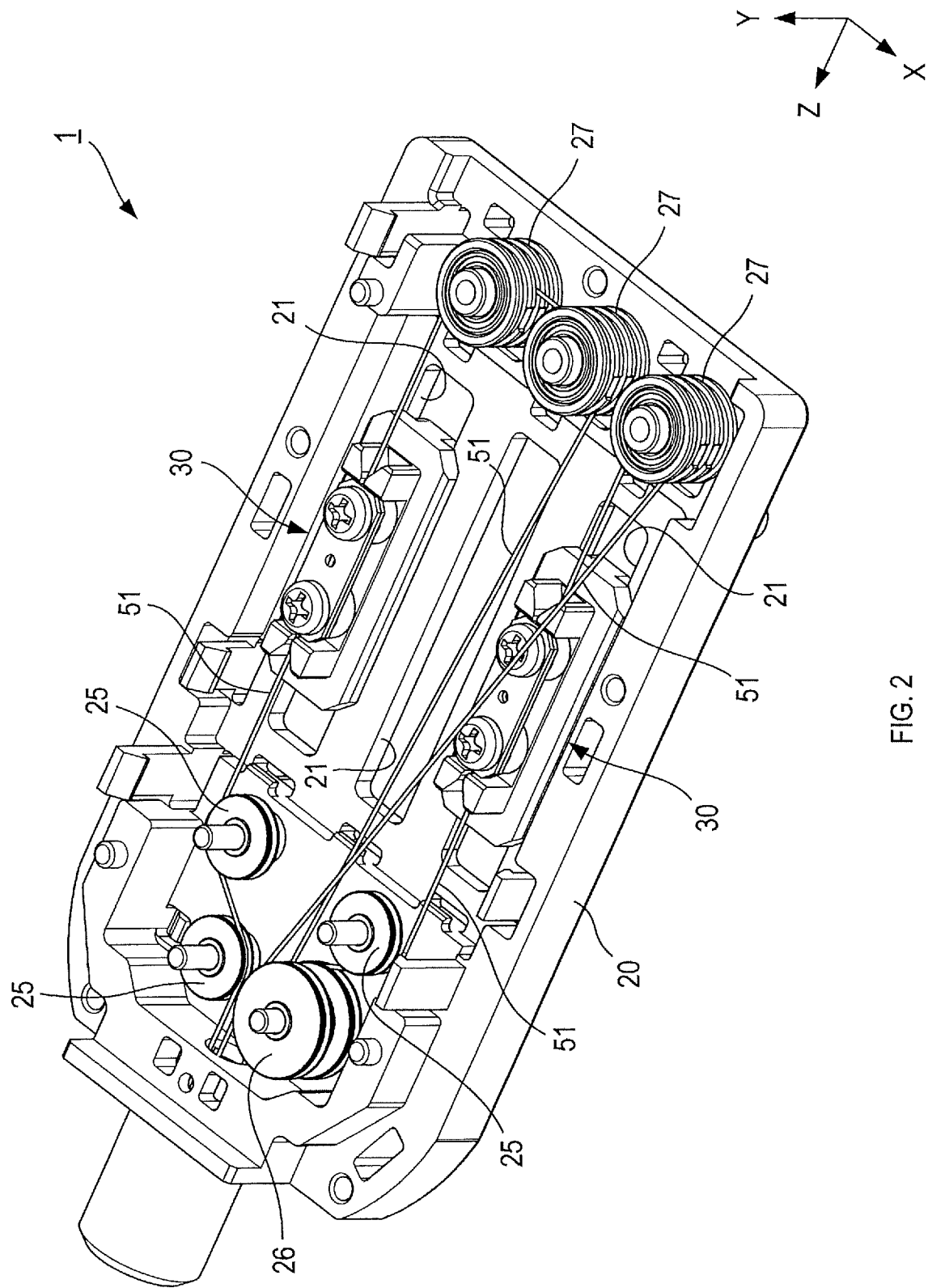
FIG. 2 is a diagram illustrating a surgical instrument body, slides, and a wire.

Note that in FIG. 2, for ease of description, only the sliders 30 and the wires 51 disposed in the driven grooves 21 at both ends in the X-axis direction are illustrated and the slider 30 and the rod 55 at the center are omitted.

As illustrated in FIG. 2, three first guide pulleys 25, one second guide pulley 26, and three third guide pulleys 27 for guiding the wires 51 to the shaft 10 are further provided inside the surgical instrument body 20.

The first guide pulley 25 is disposed at a position closer to the shaft 10 than the slider 30. Each of the three first guide pulleys 25 has one rotating disk. Among the three first guide pulleys 25, the two first guide pulleys 25 disposed on the negative direction side of the X axis guide the wire 51 extending from the slider 30 on the negative direction side of the X axis to the inside of the shaft 10.

Similarly to the first guide pulley 25, the second guide pulley 26 is disposed at a position closer to the shaft 10 than the sliders 30. The second guide pulley 26 has three rotating disks. The circumferential surfaces of the three disks are provided with grooves through which the wires 51 are guided.

One disk has a smaller diameter than the other two disks. The other two disks have the same diameter. The disk having the small diameter is disposed between the disks having a large diameter. Among the three disks of the second guide pulley 26, the disk having the large diameter and disposed on the negative direction side of the Y axis, together with the first guide pulley 25, guides the wire 51 extending from the slider 30 on the positive direction side of the X axis to the inside of the shaft 10.

The third guide pulleys 27 are disposed at a position farther from the shaft 10 than the sliders 30. The three third guide pulleys 27 are arranged side by side in the X-axis direction. The third guide pulley 27 is formed in a cylindrical shape, and a cylindrical surface thereof is provided with multiple grooves through which the wire 51 is guided.

In the present embodiment, an example in which three grooves are provided at different positions in the Y-axis direction will be described. At least the third guide pulley 27 on the positive direction side of the X axis is configured such that the wire 51 is movable from the groove, in which the wire 51 is being guided, to the adjacent groove.

Among the three third guide pulleys 27, the third guide pulley 27 on the negative direction side of the X axis and the central third guide pulley 27, together with the disk having the small diameter among the three disks of the second guide pulley 26, guide the wire 51 extending from the slider 30 on the negative direction side of the X axis to the inside of the shaft 10.

The third guide pulley 27 on the positive direction side of the X axis, together with the disk having the large diameter and disposed on the positive direction side of the Y axis among the three disks of the second guide pulley 26, guides the wire 51 extending from the slider 30 on the positive direction side of the X axis to the inside of the shaft 10.

Figure 3:
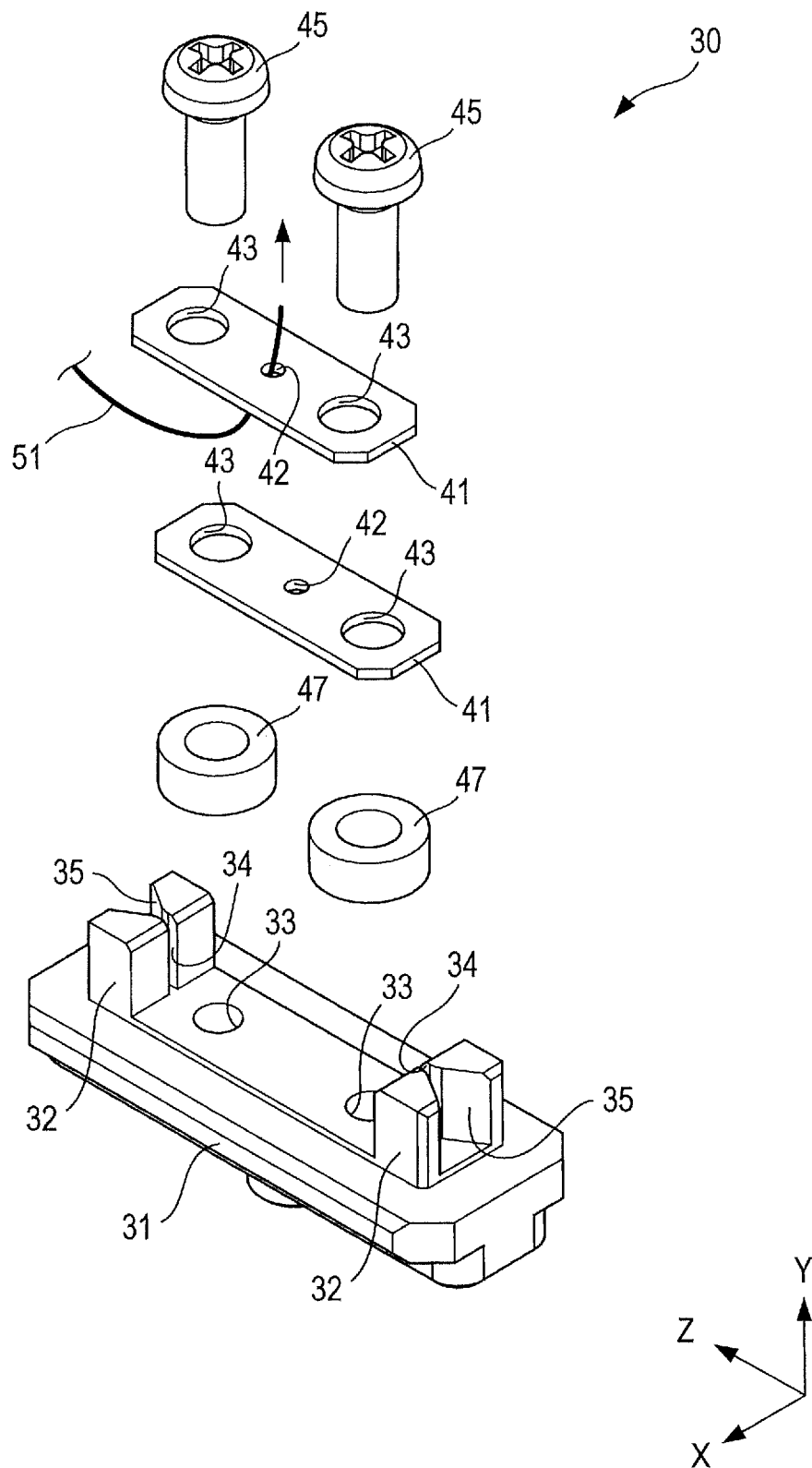
FIG. 3 is an exploded view of a slide.
Figure 4:
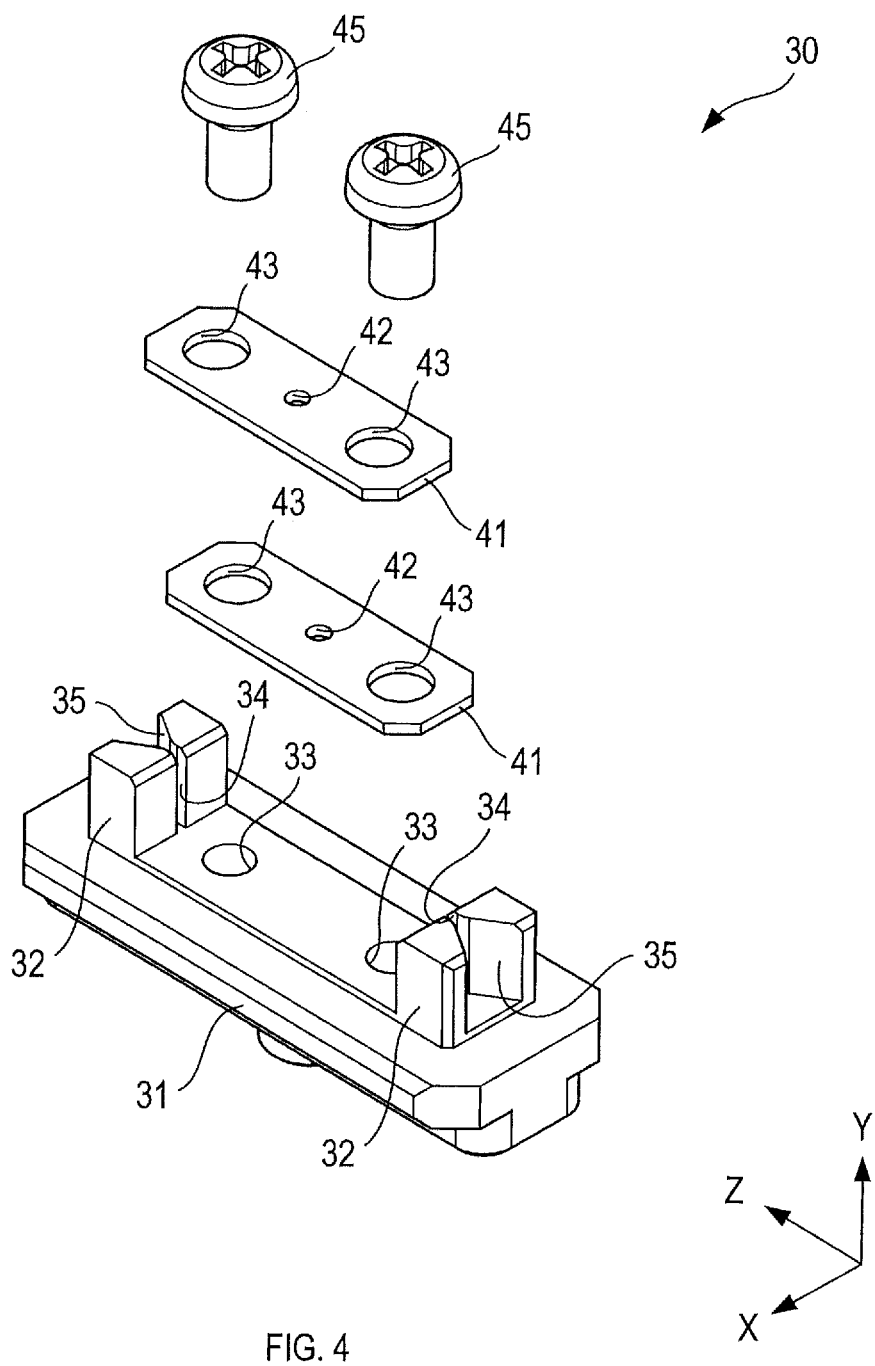
FIG. 4 is another exploded view of a slide.

As illustrated in FIGS. 3 and 4, the slider 30 is provided with at least a slider body 31, two holders 41, and fasteners 45. As illustrated in FIG. 3, the slider 30 may further include spacers 47.

For example, the slider 30 illustrated in FIG. 3 is the slider 30 disposed in the driven groove 21 on the negative direction side of the X axis, and the slider 30 illustrated in FIG. 4 is the slider 30 disposed in the driven groove 21 on the positive direction side of the X axis.

The slider body 31 is a member formed to extend in the Z-axis direction, and is configured such that the two holders 41 are attachable and detachable. The slider body 31 is provided with two protrusions 32 between which the holders 41 are disposed. Two female screw holes 33 corresponding to male screws of the fasteners 45 are provided between the two protrusions 32.

The two protrusions 32 have columnar shapes protruding in the positive Y-axis direction from a surface of the slider body 31 on the positive Y-axis direction side. One of the two protrusions 32 is provided in a region of the slider body 31 on the positive Z-axis direction side, and the other is provided in a region of the slider body 31 on the negative Z-axis direction side.

The two protrusions 32 are provided with guides 34 that guide the wire 51 to the two holders 41. The guide 34 is a groove extending in the Y-axis direction and the Z-axis direction. The guide 34 is provided in a central region of the protrusion 32 in the X-axis direction. The width of the guide 34 in the X-axis direction is large enough to dispose the wire 51 therein. In the present embodiment, the guide 34 is formed over the entire region of the protrusion 32 in the Y-axis direction.

The guide 34 is provided with an inclined part 35 in which the width of the groove is narrowed toward the two holders 41. The inclined part 35 opens on a surface of the protrusion 32 opposite to a surface facing the holder 41.

The two holders 41 are disposed on the slider body 31 and are configured to sandwich and hold the wire 51 therebetween. The holder 41 has a plate-like shape. In the present embodiment, an example in which the holder 41 is a rectangular plate member with corners cut off will be described.

The holder 41 is provided with an insertion hole 42 and a fixing hole 43.

The insertion hole 42 is a through hole through which ends of the wire 51 are inserted. It is sufficient that the insertion hole 42 be provided in at least one of the two holders 41. In the present embodiment, the insertion hole 42 is provided in a central region of the holder 41 in the Z-axis direction.

The fixing hole 43 is a through hole through which the fastener 45 is inserted. The fixing hole 43 is provided in both of the two holders 41. In the present embodiment, the two fixing holes 43 are provided side by side in the Z-axis direction with the insertion hole 42 interposed therebetween.

The fasteners 45 fix the two holders 41 so that the two holders 41 are disposed on the slider body 31 and so that the wire 51 is held between the two holders 41. In the present embodiment, an example in which the fastener 45 has a male screw will be described.

As illustrated in FIG. 3, the two spacers 47 each have a hole into which the fastener 45 is inserted. The spacers 47 are disposed between the slider body 31 and the two holders 41. A desired value can be selected as the dimension of the spacer 47 in the Y-axis direction.

Next, a method of applying a desired tension to the wire 51 in the surgical instrument 1 having the above configuration will be described.

Note that forming the wire 51 in an annular shape in the following description includes not only holding both ends of one wire 51 to form the wire in an annular shape, but also holding respective ends of two wires 51 connected to the joint 11 or the like to form the wire in an annular shape.

As illustrated in FIG. 2, the wire 51 held by the slider 30 is guided from the inside of the shaft 10 to the slider 30 via the first guide pulley 25, the second guide pulley 26, and the third guide pulley 27.

Figure 5:
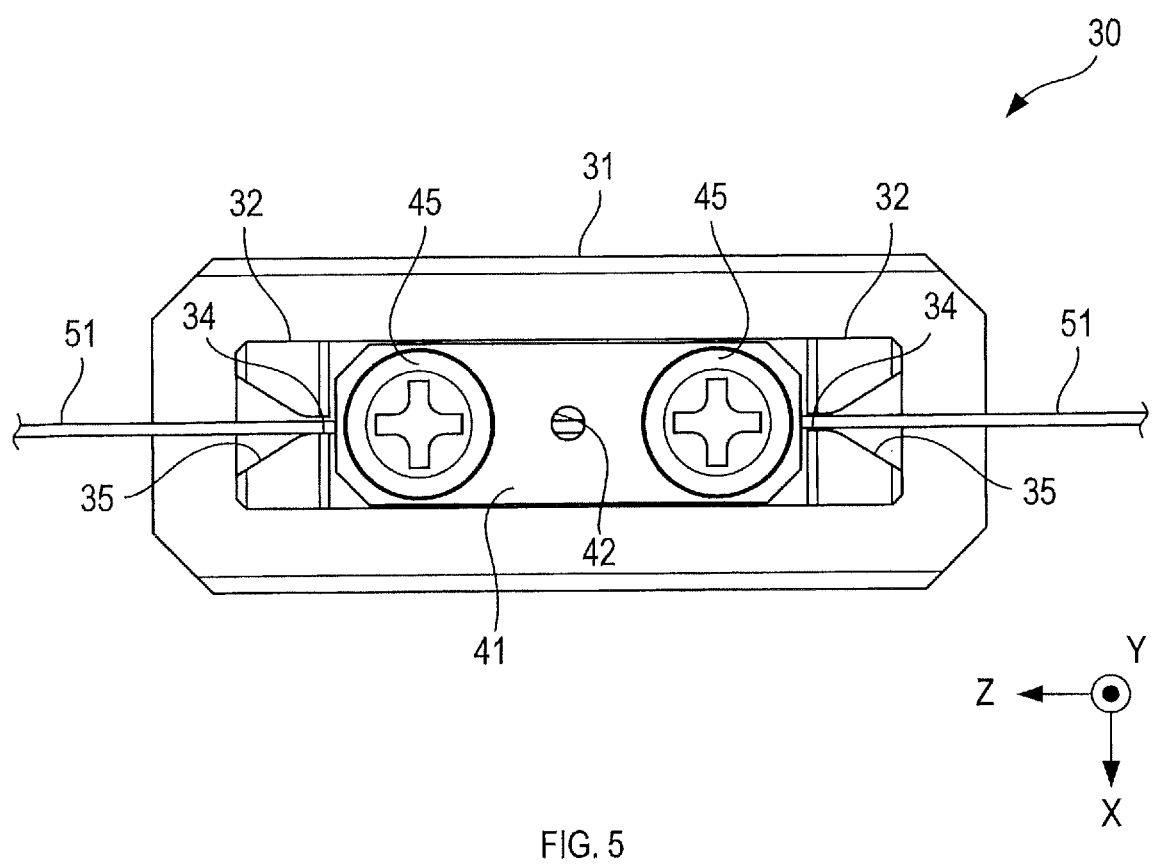
FIG. 5 is a diagram illustrating a slide and a wire.

The ends of the wire 51 are held by each of the sliders 30 disposed in the driven grooves 21 on the positive direction side and the negative direction side of the X axis. As illustrated in FIG. 5, the wire 51 is disposed so as to pass through the guides 34 and the inclined parts 35 of the protrusions 32.

The wire 51 having passed through the guide 34 and the inclined part 35 is disposed between the two holders 41 as illustrated in FIG. 3. The tip ends of the wire 51 pass through the insertion hole 42 of the holder 41 and are pulled out in the positive direction of the Y axis. At this time, the wire 51 is formed in an annular shape. In FIG. 3, only a part of the wire 51 held by the slider 30 is illustrated for ease of understanding.

The fasteners 45 are inserted into the fixing holes 43 of the holders 41. Additionally, the fasteners 45 are screwed into the female screw holes 33 of the slider body 31. The wire 51 disposed between the two holders 41 is disposed at a position avoiding the fasteners 45.

The fasteners 45 are tightened into the female screw holes 33 while a force is applied to the tip ends of the wire 51 in a direction in which the wire 51 is pulled out from the insertion hole 42. The magnitude of the applied force is such that a desired tension is applied to the annular wire 51.

When the fasteners 45 are tightened into the female screw holes 33, the wire 51 is held between the two holders 41. Additionally, the two holders 41 are fixed to the slider body 31. The wire 51 pulled out from the insertion hole 42 is processed not to interfere with the relative movement of the slider 30. For example, the wire 51 is cut at the position of the insertion hole 42.

With the surgical instrument 1 and the slider 30 having the above-described configurations, the ends of the wire 51 are inserted into the insertion hole 42 and pulled, whereby tension is applied to the annular wire 51. By bringing the two holders 41 close to each other in a state where tension is applied to the annular wire 51, the wire 51 can be held between the two holders 41. Hence, a desired tension can be applied to the annular wire 51 without providing a mechanism for applying tension to the annular wire 51, and a desired tension can be easily applied to the annular wire 51.

By providing the protrusions 32 and the guides 34, the positions of the two holders 41 relative to the slider body 31 can be easily stabilized. Further, by guiding the wire to the holder 41 using the guides 34 provided in the protrusions 32, the position of the wire relative to the holders 41 can be easily stabilized. In particular, even if the slider body 31 causes relative movement in the Z-axis direction, the position of the wire relative to the holders 41 can be easily stabilized.

By providing the inclined part 35 in the guide 34, the wire 51 can be disposed in the guide 34 easily. Additionally, it is easy to, curb an increase in stress acting on the contact portion between the wire 51 and the guide 34 when the slider body 31 causes relative movement in the Z-axis direction.

By providing the fasteners 45, it is easy to perform the work of fixing the two holders 41 at desired positions of the slider body 31 and the work of fixing the two holders 41 with the wire 51 held between the two holders 41. Additionally, both works can be performed simultaneously.

Figure 6:
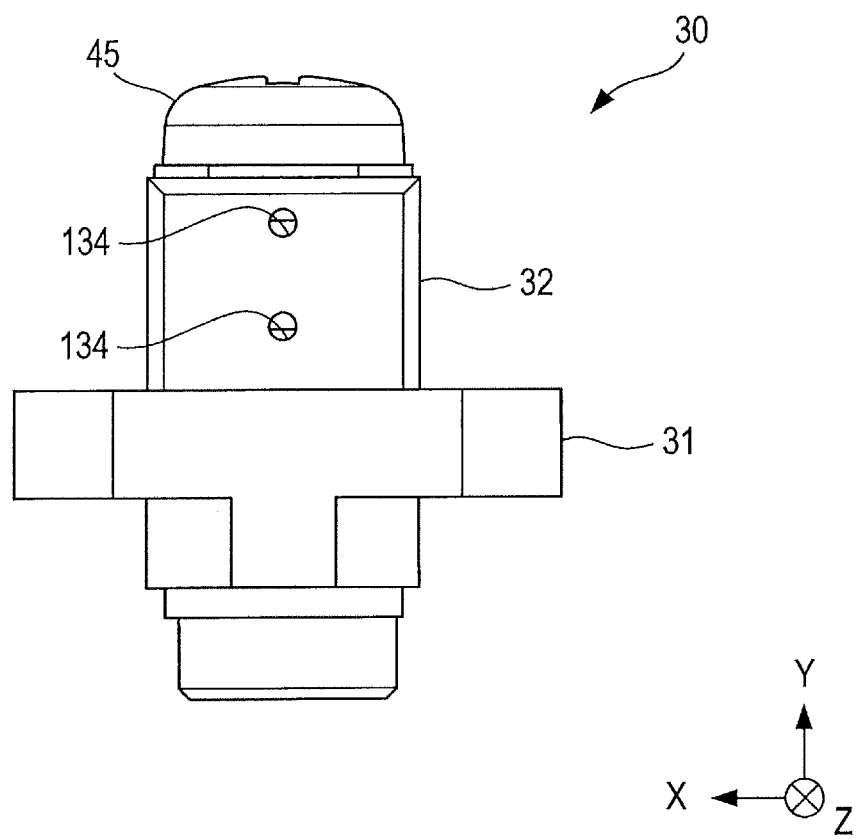
FIG. 6 is a diagram illustrating another embodiment of a slide.

Note that the guide 34 may be a groove extending in the Y-axis direction and the Z-axis direction, or may be a guide 134 which is a through hole as illustrated in FIG. 6. The guide 134 is a through hole large enough to insert the wire 51.

In FIG. 6, two guides 134 are provided to be spaced apart in the Y-axis direction in one protrusion 32. The number of the guides 134 may be one, three, or more.

Note that the technical scope of the present disclosure is not limited to the above embodiment, and various modifications can be made without departing from the gist of the present disclosure. For example, in the present embodiment, an example in which the forceps 12 are disposed on the shaft 10 of the surgical instrument 1 has been described. Alternatively, any instrument used for treatment of a patient may be disposed on the shaft 10.

The invention claimed is:

1. A slider comprising:
a slider body disposed to be movable in a linear direction within a groove of a surgical instrument body according to an actuating force transmitted from outside the surgical instrument body; and
two holders disposed on the slider body for holding ends of a wire wound along the surgical instrument body between the two holders to retain the wire under tension, wherein
at least a first holder of the two holders is provided with an insertion hole for inserting and passing the ends of the wire toward an outside from between the two holders to generate tension in the wire.

2. The slider according to claim 1 further comprising:
two protrusions protruding from the slider body to a side where the two holders are disposed, the two holders being disposed between the two protrusions; and
a guide provided in the protrusion for guiding the wire to the two holders.

3. The slider according to claim 2, wherein
the guide has the shape of a groove, which is formed in the protrusion and which extends toward the two holders, and
the guide is provided with an inclined part, in which a width of the groove narrows toward the two holders.

4. The slider according to claim 3, further comprising a fastener for fixing the two holders so that the two holders are disposed on the slider body and so that the wire is held between the two holders.

5. The slider according to claim 2, further comprising a fastener for fixing the two holders so that the two holders are disposed on the slider body and so that the wire is held between the two holders.

6. The slider according to claim 1, further comprising a fastener for fixing the two holders so that the two holders are disposed on the slider body and so that the wire is held between the two holders.

7. A surgical instrument comprising:
the slider according to claim 1;
a surgical instrument body that accommodates the slider; and
a movable part driven by a driving force transmitted by the slider.

8. A slider comprising:
a slider body positioned within a groove of a surgical instrument body and configured to move according to an actuating force transmitted from outside the surgical instrument body, the slider body having a plurality of through holes; and
two holders stacked together on a surface of the slider body, each holder of the two holders having a plurality of through holes being aligned with the plurality of through holes of the slider body;
wherein at least one holder of the two holders comprises an insertion hole configured to receive a wire wound along the surgical instrument body and generate tension in the wire.

9. The slider according to claim 8, further comprising:
two protrusions disposed on the surface of the slider body, the two holders being positioned between the two protrusions; and
a guide provided in each of the two protrusions.

10. The slider according to claim 9, wherein
the guide has a groove shape that narrows as a distance from the two holders decreases.

11. The slider according to claim 10, further comprising a plurality of fasteners, each fastener being insertable through a respective one of the plurality of through holes of the two holders and a corresponding one of the plurality of through holes of the slider body.

12. The slider according to claim 9, further comprising a plurality of fasteners, each fastener being insertable through a respective one of the plurality of through holes of the two holders and a corresponding one of the plurality of through holes of the slider body.

13. The slider according to claim 8, further comprising a plurality of fasteners, each fastener being insertable through a respective one of the plurality of through holes of the two holders and a corresponding one of the plurality of through holes of the slider body.

14. A surgical instrument comprising:
the slider according to claim 8;
a surgical instrument body configured to accommodate the slider; and
a movable part disposed at a distal end of the surgical instrument body.

15. A slider comprising:
a slider body configured to be linearly movable in a linear direction within a groove of a surgical instrument body according to an actuating force transmitted from outside the surgical instrument body; and
two plates disposed on the slider body to retain a wire wound along the surgical instrument body under tension therebetween,
wherein at least a first plate of the two plates comprises an insertion hole for inserting and passing ends of the wire toward an outside of the slider from between the two plates to generate tension in the wire.

16. The slider according to claim 15, further comprising:
two protrusions protruding from the slider body to a side of the slider body on which the two plates are disposed, the two plates being disposed between the two protrusions
wherein each of the two protrusions comprises a guide through which the wire passes.

17. The slider according to claim 16, wherein:
each guide has a groove shape that narrows as a distance from the two plates decreases.

18. The slider according to claim 16, further comprising a fastener that fixes the two plates to the slider body to hold the wire between the two plates.

19. The slider according to claim 15, further comprising a fastener that fixes the two plates to the slider body to hold the wire between the two plates.

20. A surgical instrument comprising:
the slider according to claim 15;
a body that accommodates the slider; and
a movable part driven by a driving force transmitted by the slider.

\* \* \* \* \*